(12) United States Patent
Batista et al.

(10) Patent No.: US 12,115,307 B2
(45) Date of Patent: *Oct. 15, 2024

(54) AEROSOL-GENERATING SYSTEM WITH MOTOR

(71) Applicant: Altria Client Services LLC, Richmond, VA (US)

(72) Inventors: Rui Nuno Batista, Morges (CH); Ben Mazur, Bristol (GB)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,398

(22) Filed: Apr. 4, 2023

(65) Prior Publication Data

US 2023/0239968 A1 Jul. 27, 2023

Related U.S. Application Data

(63) Continuation of application No. 16/821,111, filed on Mar. 17, 2020, now Pat. No. 11,641,695, which is a
(Continued)

(30) Foreign Application Priority Data

Dec. 22, 2015 (EP) .................................... 15202139

(51) Int. Cl.
*A61M 15/06* (2006.01)
*A24F 40/10* (2020.01)
(Continued)

(52) U.S. Cl.
CPC ............ *A61M 15/06* (2013.01); *A24F 40/42* (2020.01); *A24F 40/48* (2020.01); *H05B 1/0244* (2013.01);
(Continued)

(58) Field of Classification Search
None
See application file for complete search history.

(56) References Cited

U.S. PATENT DOCUMENTS 5,743,251 A 4/1998 Howell et al.
6,063,339 A * 5/2000 Tisone .................. B05B 1/3053
422/65
(Continued)

FOREIGN PATENT DOCUMENTS

CN 101522244 A 9/2009
CN 104684422 A 6/2015
(Continued)

OTHER PUBLICATIONS

Canadian Office Action dated Aug. 21, 2023 for corresponding Canadian Application No. 3005687.
(Continued)

*Primary Examiner* — Thor S Campbell
(74) *Attorney, Agent, or Firm* — Harness, Dickey & Pierce, P.L.C.

(57) ABSTRACT

An aerosol-generating system may include a liquid storage portion configured to hold aerosol-forming substrate, a vaporizer, and a pump. The liquid storage portion includes a movable wall and an outlet. The vaporizer includes a heating element having a structure that at least partially defines an internal passage. The pump may deliver liquid aerosol-forming substrate from the outlet of the liquid storage portion to the internal passage of the heating element. The pump may include a micro stepper motor with a drive shaft that is configured to rotate a particular amount based on performing an individual step, a piston connected to the movable wall, and a lead screw connecting the drive shaft to the piston and configured to translate rotation of the drive shaft into axial movement of the piston and the
(Continued)

movable wall. The vaporizer may at least partially vaporize the delivered liquid aerosol-forming substrate.

14 Claims, 4 Drawing Sheets

Related U.S. Application Data continuation of application No. 15/388,644, filed on Dec. 22, 2016, now Pat. No. 10,624,392, which is a continuation of application No. PCT/EP2016/079944, filed on Dec. 6, 2016.

(51) Int. Cl.
| | |
|---|---|
| *A24F 40/42* | (2020.01) |
| *A24F 40/48* | (2020.01) |
| *H05B 1/02* | (2006.01) |
| *A24F 15/015* | (2020.01) |
| *A24F 40/44* | (2020.01) |
| *A24F 40/46* | (2020.01) |
| *A24F 40/485* | (2020.01) |

(52) U.S. Cl.
CPC ............ *A24F 15/015* (2020.01); *A24F 40/10* (2020.01); *A24F 40/44* (2020.01); *A24F 40/46* (2020.01); *A24F 40/485* (2020.01); *H05B 2203/021* (2013.01); *H05B 2203/022* (2013.01)

(56) References Cited

U.S. PATENT DOCUMENTS

| | | | | |
|---|---|---|---|---|
| 8,499,766 B1* | 8/2013 | Newton | ................ | A24F 40/51 |
| | | | | 131/273 |
| 9,067,029 B2* | 6/2015 | Yamada | ................ | A61M 15/00 |
| 9,603,386 B2* | 3/2017 | Xiang | ................ | A24F 40/50 |
| 9,675,114 B2* | 6/2017 | Timmermans | .......... | A24F 40/60 |
| 9,808,032 B2* | 11/2017 | Yamada | ............... | A61M 11/042 |
| 10,624,392 B2* | 4/2020 | Batista | .................. | A24F 40/48 |
| 2003/0132219 A1* | 7/2003 | Cox | .................. | A61M 15/025 |
| | | | | 392/397 |
| 2004/0081624 A1* | 4/2004 | Nguyen | ............. | A61M 15/008 |
| | | | | 424/44 |
| 2004/0195403 A1* | 10/2004 | Atterbury | ............. | A61M 15/02 |
| | | | | 239/690 |
| 2005/0034723 A1* | 2/2005 | Bennett | .................. | A61K 9/007 |
| | | | | 128/203.12 |
| 2007/0283972 A1* | 12/2007 | Monsees | ................ | A24F 42/10 |
| | | | | 131/273 |
| 2008/0038363 A1* | 2/2008 | Zaffaroni | ............. | A61M 11/041 |
| | | | | 424/502 |
| 2009/0095287 A1* | 4/2009 | Emarlou | ............. | A61M 15/06 |
| | | | | 128/200.14 |
| 2009/0133691 A1* | 5/2009 | Yamada | ............... | A61M 11/005 |
| | | | | 128/200.16 |
| 2010/0181387 A1* | 7/2010 | Zaffaroni | ............. | A61M 11/042 |
| | | | | 239/128 |
| 2010/0313901 A1* | 12/2010 | Fernando | ............. | H02J 7/0042 |
| | | | | 131/330 |
| 2011/0036346 A1* | 2/2011 | Cohen | .................. | A24F 40/60 |
| | | | | 128/200.14 |
| 2012/0048266 A1* | 3/2012 | Alelov | ................ | A61M 15/06 |
| | | | | 128/203.14 |
| 2012/0090630 A1* | 4/2012 | Hon | .................. | A24F 40/60 |
| | | | | 131/273 |
| 2013/0042865 A1* | 2/2013 | Monsees | ............... | A61M 15/06 |
| | | | | 128/203.27 |
| 2013/0104916 A1* | 5/2013 | Bellinger | ............. | A61M 11/042 |
| | | | | 131/328 |
| 2013/0284192 A1* | 10/2013 | Peleg | .................. | A24F 40/53 |
| | | | | 131/329 |
| 2013/0319440 A1* | 12/2013 | Capuano | ................ | A24F 40/50 |
| | | | | 131/329 |
| 2013/0340775 A1* | 12/2013 | Juster | .................. | H04L 12/1827 |
| | | | | 131/273 |
| 2014/0053856 A1* | 2/2014 | Liu | ......................... | A24F 40/51 |
| | | | | 131/329 |
| 2014/0060554 A1* | 3/2014 | Collett | .................... | A24F 40/30 |
| | | | | 392/386 |
| 2014/0107815 A1* | 4/2014 | LaMothe | ................. | A24F 15/01 |
| | | | | 700/90 |
| 2014/0123989 A1* | 5/2014 | LaMothe | .......... | A61M 15/0003 |
| | | | | 131/328 |
| 2014/0123990 A1* | 5/2014 | Timmermans | .......... | A24F 40/60 |
| | | | | 131/328 |
| 2014/0174459 A1* | 6/2014 | Burstyn | .................. | A24F 40/60 |
| | | | | 131/273 |
| 2014/0224267 A1* | 8/2014 | Levitz | ...................... | A24F 40/40 |
| | | | | 320/108 |
| 2014/0246035 A1* | 9/2014 | Minskoff | ................. | A24F 40/65 |
| | | | | 131/329 |
| 2014/0251324 A1* | 9/2014 | Xiang | ..................... | A24F 40/50 |
| | | | | 128/202.21 |
| 2014/0283855 A1* | 9/2014 | Hawes | .................... | A24F 40/48 |
| | | | | 131/328 |
| 2014/0305820 A1* | 10/2014 | Xiang | ..................... | A24F 40/95 |
| | | | | 206/236 |
| 2014/0334804 A1* | 11/2014 | Choi | ..................... | A24F 40/485 |
| | | | | 392/404 |
| 2014/0360512 A1* | 12/2014 | Xiang | ................. | H02J 7/00712 |
| | | | | 131/328 |
| 2015/0047662 A1* | 2/2015 | Hopps | ................... | A61M 15/06 |
| | | | | 392/394 |
| 2015/0053217 A1* | 2/2015 | Steingraber | ............. | A24F 40/50 |
| | | | | 131/329 |
| 2015/0075546 A1* | 3/2015 | Kueny, Sr. | ............... | A24F 40/65 |
| | | | | 700/299 |
| 2015/0114409 A1 | 4/2015 | Brammer et al. | | |
| 2015/0117842 A1 | 4/2015 | Brammer et al. | | |
| 2015/0122252 A1* | 5/2015 | Frija | ....................... | A24F 40/65 |
| | | | | 128/202.21 |
| 2015/0173124 A1* | 6/2015 | Qiu | ......................... | A24F 40/60 |
| | | | | 131/328 |
| 2015/0216237 A1 | 8/2015 | Wensley et al. | | |
| 2015/0224268 A1* | 8/2015 | Henry | ...................... | G06Q 50/01 |
| | | | | 128/202.21 |
| 2015/0237917 A1* | 8/2015 | Lord | ....................... | G01L 19/04 |
| | | | | 131/328 |
| 2015/0245661 A1* | 9/2015 | Milin | ...................... | A24F 40/40 |
| | | | | 131/329 |
| 2015/0257445 A1* | 9/2015 | Henry, Jr. | ............... | A24F 40/50 |
| | | | | 131/328 |
| 2015/0257448 A1* | 9/2015 | Lord | .................... | H05B 1/0244 |
| | | | | 700/90 |
| 2015/0258289 A1* | 9/2015 | Henry, Jr. | ............... | A24F 40/50 |
| | | | | 128/202.21 |
| 2015/0288468 A1* | 10/2015 | Xiang | ..................... | A24F 40/65 |
| | | | | 455/500 |
| 2015/0320116 A1* | 11/2015 | Bleloch | .................. | A24F 40/44 |
| | | | | 219/628 |
| 2015/0357839 A1* | 12/2015 | Cai | ..................... | H02J 7/00714 |
| | | | | 131/329 |
| 2015/0359263 A1* | 12/2015 | Bellinger | ................ | A24F 40/53 |
| | | | | 392/394 |
| 2016/0007651 A1* | 1/2016 | Ampolini | ................. | A24F 40/65 |
| | | | | 131/328 |
| 2016/0021930 A1* | 1/2016 | Minskoff | ................. | A24F 40/51 |
| | | | | 392/395 |
| 2016/0106156 A1* | 4/2016 | Qiu | ...................... | H02J 7/00712 |
| | | | | 392/404 |
| 2016/0150828 A1* | 6/2016 | Goldstein | ................ | H05B 6/36 |
| | | | | 392/387 |
| 2016/0219938 A1* | 8/2016 | Mamoun | ................ | G05B 15/02 |
| 2016/0285983 A1* | 9/2016 | Liu | ........................ | G16H 40/67 |
| 2016/0331024 A1* | 11/2016 | Cameron | ................ | A24F 40/50 |
| 2016/0331026 A1* | 11/2016 | Cameron | ................ | A24F 40/50 |
| 2016/0331027 A1* | 11/2016 | Cameron | ................ | B05B 15/40 |
| 2016/0331035 A1* | 11/2016 | Cameron | ................ | H04M 1/21 |
| 2016/0331859 A1* | 11/2016 | Cameron | ................ | A24F 40/51 |

(56) References Cited

U.S. PATENT DOCUMENTS

| | | | |
|---|---|---|---|
| 2016/0337362 A1* | 11/2016 | Cameron | G06Q 20/3278 |
| 2016/0338407 A1* | 11/2016 | Kerdemelidis | A24F 40/60 |
| 2016/0345628 A1* | 12/2016 | Sabet | H04M 1/21 |
| 2016/0360786 A1* | 12/2016 | Bellinger | A24F 40/46 |
| 2016/0363917 A1* | 12/2016 | Blackley | G06F 3/0488 |
| 2016/0374401 A1* | 12/2016 | Liu | A24F 40/50 131/328 |
| 2017/0020192 A1* | 1/2017 | Fregonese | A24F 40/485 |
| 2017/0042230 A1* | 2/2017 | Cameron | A24F 40/60 |
| 2017/0042231 A1* | 2/2017 | Cameron | A24F 40/65 |
| 2017/0045994 A1* | 2/2017 | Murison | A61M 15/06 |
| 2017/0046357 A1* | 2/2017 | Cameron | A24F 40/30 |
| 2017/0046738 A1* | 2/2017 | Cameron | A24F 40/65 |
| 2017/0055588 A1* | 3/2017 | Cameron | A61M 15/06 |
| 2017/0064999 A1* | 3/2017 | Perez | A24F 40/40 |
| 2017/0079327 A1* | 3/2017 | Wu | H02J 7/007 |
| 2017/0079329 A1* | 3/2017 | Zitzke | H05B 1/0225 |
| 2017/0086496 A1* | 3/2017 | Cameron | B25F 1/04 |
| 2017/0086497 A1* | 3/2017 | Cameron | H05B 1/0244 |
| 2017/0086503 A1* | 3/2017 | Cameron | A24F 40/40 |
| 2017/0086504 A1* | 3/2017 | Cameron | A24F 40/48 |
| 2017/0086505 A1* | 3/2017 | Cameron | H01L 29/78693 |
| 2017/0086507 A1* | 3/2017 | Rado | H05B 3/44 |
| 2017/0091490 A1* | 3/2017 | Cameron | G06F 21/84 |
| 2017/0092106 A1* | 3/2017 | Cameron | A24F 40/65 |
| 2017/0093960 A1* | 3/2017 | Cameron | H04W 4/80 |
| 2017/0093981 A1* | 3/2017 | Cameron | A24F 40/65 |
| 2017/0119058 A1* | 5/2017 | Cameron | A24B 15/167 |
| 2017/0127727 A1* | 5/2017 | Davidson | A61K 36/185 |
| 2017/0135400 A1* | 5/2017 | Liu | A24F 40/53 |
| 2017/0135407 A1* | 5/2017 | Cameron | A24F 40/60 |
| 2017/0135408 A1* | 5/2017 | Cameron | A24F 40/51 |
| 2017/0135409 A1* | 5/2017 | Cameron | A24F 1/02 |
| 2017/0135410 A1* | 5/2017 | Cameron | H05B 3/12 |
| 2017/0135411 A1* | 5/2017 | Cameron | A24F 40/50 |
| 2017/0135412 A1* | 5/2017 | Cameron | A24F 40/51 |
| 2017/0136193 A1* | 5/2017 | Cameron | A24F 40/48 |
| 2017/0136194 A1* | 5/2017 | Cameron | A24F 40/05 |
| 2017/0136301 A1* | 5/2017 | Cameron | A24F 40/65 |
| 2017/0143917 A1* | 5/2017 | Cohen | A24F 40/40 |
| 2017/0150756 A1* | 6/2017 | Rexroad | H05B 1/0244 |
| 2017/0157341 A1* | 6/2017 | Pandya | A61M 11/042 |
| 2017/0181467 A1* | 6/2017 | Cameron | A63F 13/98 |
| 2017/0181474 A1* | 6/2017 | Cameron | A24B 15/167 |
| 2017/0181475 A1* | 6/2017 | Cameron | A24F 40/53 |
| 2017/0185364 A1* | 6/2017 | Cameron | G09G 5/12 |
| 2017/0196270 A1* | 7/2017 | Vick | H02J 7/0042 |
| 2017/0208867 A1* | 7/2017 | Li | G08C 17/02 |
| 2017/0215480 A1* | 8/2017 | Qiu | A24F 40/65 |
| 2017/0224020 A1* | 8/2017 | Fernando | H02J 7/0042 |
| 2017/0231280 A1* | 8/2017 | Anton | A24F 40/65 392/404 |
| 2017/0245550 A1* | 8/2017 | Freelander | A61M 15/0051 |
| 2017/0245554 A1* | 8/2017 | Perez | H05B 1/0244 |
| 2017/0251719 A1* | 9/2017 | Cyphert | A24F 1/00 |
| 2017/0258136 A1* | 9/2017 | Hawes | A24F 40/53 |
| 2017/0258142 A1* | 9/2017 | Hatton | A24F 40/51 |
| 2017/0259170 A1* | 9/2017 | Bowen | A24F 40/60 |
| 2017/0273357 A1* | 9/2017 | Barbuck | H05B 3/04 |
| 2017/0280779 A1* | 10/2017 | Qiu | G05D 23/1919 |
| 2017/0290998 A1* | 10/2017 | Poston | A61M 11/047 |
| 2017/0295844 A1* | 10/2017 | Thevenaz | A24F 40/46 |
| 2017/0303590 A1* | 10/2017 | Cameron | A24F 40/00 |
| 2017/0303593 A1* | 10/2017 | Cameron | A24F 40/60 |
| 2017/0303594 A1* | 10/2017 | Cameron | A61M 15/00 |
| 2017/0309091 A1* | 10/2017 | Cameron | G07C 5/085 |
| 2017/0332702 A1* | 11/2017 | Cameron | A24F 40/65 |
| 2018/0070639 A1* | 3/2018 | Chen | F22B 1/281 |
| 2018/0184712 A1* | 7/2018 | Fraser | A24F 40/44 |
| 2018/0192700 A1* | 7/2018 | Fraser | A24F 40/42 |
| 2018/0199627 A1* | 7/2018 | Bowen | A24F 40/46 |
| 2019/0124979 A1* | 5/2019 | Sebastian | A24D 1/20 |
| 2019/0200677 A1* | 7/2019 | Chong | A24D 1/20 |
| 2019/0230987 A1* | 8/2019 | Wu | H05B 6/36 |
| 2020/0214346 A1* | 7/2020 | Batista | H05B 1/0244 |
| 2023/0239968 A1* | 7/2023 | Batista | A61M 15/0041 392/403 |

FOREIGN PATENT DOCUMENTS

| | | |
|---|---|---|
| EP | 0957959 A2 | 11/1999 |
| EP | 2047880 A1 | 4/2009 |
| JP | 2000-510763 A | 8/2000 |
| RU | 2411047 C2 | 2/2011 |
| WO | WO-97/42993 A2 | 11/1997 |
| WO | WO-2008/015918 A1 | 2/2008 |
| WO | WO-2013/027249 A1 | 2/2013 |
| WO | WO-2014150552 A1 | 9/2014 |
| WO | WO-2014153515 A1 | 9/2014 |

OTHER PUBLICATIONS

Korean Office Action dated Aug. 8, 2023 for corresponding Korean Application No. 10-2018-7015931 and English translation thereof.

Extended European Search Report, Application No. 15202139.0-1662 dated Mar. 4, 2016.

International Preliminary Report on Patentability dated Jun. 26, 2018 issued in corresponding International Application No. PCT/EP2016/079944.

International Search Report and Written Opinion dated Feb. 22, 2017 issued in corresponding International Application No. PCT/EP2016/079944.

Written Opinion of the International Searching Authority dated Jun. 26, 2018 for corresponding International Application No. PCT/EP2016/079944.

Russian Notice of Allowance and Search Report dated Mar. 11, 2020 for corresponding Russian Application No. 2018126791.

European Office Action dated Sep. 25, 2020 for corresponding European Application No. 16809733.5.

Office Action dated Nov. 30, 2020 issued in corresponding Japanese Patent Application No. 2018-529112.

Chinese Office Action dated Apr. 15, 2021 for corresponding Chinese Application No. 201680072365.2, and English-language translation thereof.

European Communication dated May 11, 2021 for corresponding European Application No. 16809733.5.

Japanese Office Action dated May 10, 2021 for corresponding Japanese Application No. 2018-529112, and English-language translation thereof.

Office Action for European Application No. 16809733.5 dated Jul. 16, 2021.

Israeli Office Action dated Jul. 4, 2021 for corresponding Israeli Application No. 259244, and English-language translation thereof.

Japanese Preappeal Review Report dated Sep. 2, 2021 for corresponding Japanese Application No. 2018-529112, and English-language translation thereof.

Israeli Notice of Allowance dated Nov. 7, 2021 for corresponding Israeli Application No. 259244.

European Communication dated Dec. 8, 2021 for corresponding European Application No. 16809733.5.

Chinese Office Action dated Dec. 30, 2021 for corresponding Chinese Application No. 201680072365.2, and English-language translation thereof.

Japanese Office Action dated Mar. 22, 2022 for corresponding Japanese Application No. 2018-529112, and English-language translation thereof.

Mexican Office Action dated May 12, 2022 for corresponding Mexican Application No. MX/a/2018/007402.

Japanese Decision on Appeal dated Jul. 13, 2022 for corresponding Japanese Application No. 2018-529112, and English-language translation thereof.

Chinese Office Action dated Jul. 19, 2022 for corresponding Chinese Application No. 201680072365.2.

Canadian Office Action dated Jan. 13, 2023 for corresponding Canadian Application No. 3005687.

(56) References Cited

OTHER PUBLICATIONS

Korean Notice of Allowance dated Feb. 21, 2024 for corresponding Korean Application No. 10-2018-7015931 and English translation thereof.

\* cited by examiner

AEROSOL-GENERATING SYSTEM WITH MOTOR

CROSS-REFERENCE TO RELATED APPLICATIONS

This application is a continuation of U.S. application Ser. No. 16/821,111, filed on Mar. 17, 2020, which is continuation of U.S. application Ser. No. 15/388,644, filed on Dec. 22, 2016, which is a continuation of, and claims priority to, international application no. PCT/EP2016/079944, filed on Dec. 6, 2016, and further claims priority under 35 U.S.C. § 119 to European Patent Application No. 15202139.0, filed Dec. 22, 2015, the entire contents of each of which are incorporated herein by reference.

BACKGROUND

Field

One or more example embodiments relate to aerosol-generating systems, including handheld electrically operated vaping systems, also referred to as electronic vaping devices. In particular, one or more example embodiments relate to aerosol-generating systems in which the aerosol-forming substrate is liquid and is contained in a liquid storage portion.

Description of Related Art

Some aerosol-generating systems include a device portion comprising a battery and control electronics, a cartridge portion comprising a supply of aerosol-forming substrate held in a liquid storage portion, and an electrically operated vaporizer. A cartridge may include both a supply of aerosol-forming substrate held in the liquid storage portion and a vaporizer. Such a cartridge may be sometimes referred to as a "cartomizer". The vaporizer typically comprises a coil of heater wire wound around an elongate wick soaked in the liquid aerosol-forming substrate held in the liquid storage portion. The cartridge portion may include, in addition to the supply of aerosol-forming substrate and an electrically operated vaporizer, an outlet-end insert, via which an adult vaper may draw a vapor generated by the vaporizer.

EP 0 957 959 B1 discloses an electrically operated aerosol generator for receiving liquid material from a source, the aerosol generator comprising a pump for pumping the liquid material in metered amounts from the source through a tube with an open end, and a heater surrounding the tube. When heating the liquid material by the heater, the volatized material expands by exiting the open end of the tube.

Residues are created upon heating. In capillary tubes, the residues can cause clogging. This effect can alter liquid transport properties. Furthermore, the liquid material is heated indirectly: First the tube or a capillary wick is heated which in turn heats the liquid material. Heat can therefore be lost during the energy transfer process.

It would be desirable to provide an improved aerosol-generating system with a low-maintenance liquid transport system and reduced power consumption.

SUMMARY

According to some example embodiments, an aerosol-generating system may include: a liquid storage portion configured to store a liquid aerosol-forming substrate, wherein the liquid storage portion includes a movable wall and an outlet; a vaporizer comprising a heating element having a structure defining an open-ended internal passage; and a pump configured to deliver liquid aerosol-forming substrate from the outlet of the liquid storage portion to the open-ended internal passage of the heating element. The pump may include a micro stepper motor with a drive shaft that is configured to rotate for a particular amount upon performing one step of the micro stepper motor; a piston connected to the movable wall; and a lead screw connecting the drive shaft to the piston and configured to translate a rotation of the drive shaft into an axial movement of the piston and a corresponding axial movement of the movable wall. The aerosol-generating system may include a power supply configured to supply electrical power to the vaporizer and the pump.

The liquid storage portion and pump may be collectively configured to cause a particular amount of liquid aerosol-forming substrate to be delivered from the outlet of the liquid storage portion to the open-ended internal passage of the heating element upon performing one step of the micro stepper motor, based on the axial movement of the movable wall towards the liquid storage portion causing a reduction of a volume of the liquid storage portion.

The micro stepper motor may be further configured to perform a step in a reverse direction, such that an internal volume of the liquid storage portion is increased.

The movable wall may be configured to contain the liquid aerosol-forming substrate in the liquid storage portion so that the micro stepper motor and the piston are not in contact with the liquid aerosol-forming substrate.

The aerosol-generating system may include a chamber configured to receive the liquid aerosol-forming substrate. The heating element may be located inside the chamber proximate to the outlet of the liquid storage portion.

The aerosol-generating system may include a tubing segment configured to direct the liquid aerosol-forming substrate from the liquid storage portion to the vaporizer.

The vaporizer may be located proximate to an open end of the tubing segment.

The tubing segment may include a capillary tube.

The vaporizer may include a heating coil extending around the tubing segment.

The vaporizer may include a conical heater extending from the tubing segment along a longitudinal axis of at least the tubing segment.

The liquid storage portion may include a one-way valve connected to the outlet of the liquid storage portion.

The outlet of the liquid storage portion may be configured to direct a flow of the liquid aerosol-forming substrate having a flow rate that is within about 0.5 microliters per second to about 2 microliters per second.

The aerosol-generating system may include a main assembly and a cartridge. The cartridge may be configured to be removably coupled to the main assembly. The main assembly may include the power supply and the micro stepper motor. The cartridge may include the liquid storage portion.

The cartridge may include the liquid storage portion, the piston, and the lead screw.

The aerosol-generating system may include a first cover that is configured to cover at least one of the movable wall of the liquid storage portion, the piston, and the lead screw prior to the cartridge being inserted into the main assembly.

The aerosol-generating system may include a second cover that is configured to cover the outlet of the liquid storage portion prior to the cartridge being inserted into the main assembly.

According to some example embodiments, a method for generating aerosol may include: storing liquid aerosol-forming substrate in a liquid storage portion, the liquid storage portion including a movable wall and an outlet; delivering liquid aerosol-forming substrate from the outlet of the liquid storage portion to an open-ended internal passage defined by a heating element of a vaporizer; and heating the delivered liquid aerosol-forming substrate at the open-ended internal passage to at least partially vaporize the delivered liquid aerosol-forming substrate. The delivering may include actuating a micro stepper motor to perform one step, such that a drive shaft of the micro stepper motor is rotated for a particular amount, wherein a lead screw is connected to the drive shaft, the lead screw is connected to a piston, the piston is connected to the movable wall such that a rotation of the drive shaft is translated into an axial movement of the piston and a corresponding axial movement of the movable wall.

Actuating the micro stepper motor to perform one step causes a particular amount of liquid aerosol-forming substrate to be delivered from the outlet of the liquid storage portion, based on the axial movement of the movable wall towards the liquid storage portion causing a reduction of a volume of the liquid storage portion.

The method may include causing the micro stepper motor to perform a step in a reverse direction, such that an internal volume of the liquid storage portion is increased.

According to some example embodiments, a cartridge for an aerosol-generating system may include: a liquid storage portion configured to store a liquid aerosol-forming substrate. The liquid storage portion may include a movable wall and an outlet. The cartridge may be configured to be coupled to a main assembly such that the outlet of the liquid storage portion is configured to direct a flow of liquid aerosol-forming substrate from the liquid storage portion to a vaporizer of the main assembly. The liquid storage portion may be configured to engage with a pump at the movable wall, such that the movable wall is configured to be moved based on operation of the pump to cause liquid aerosol-forming substrate to be conveyed out of the liquid storage portion through the outlet of the liquid storage portion.

The movable wall may be configured to contain the liquid aerosol-forming substrate in the liquid storage portion to isolate the liquid aerosol-forming substrate from at least a portion of the pump.

The outlet of the liquid storage portion may be configured to direct a flow of the liquid aerosol-forming substrate such that the flow of liquid aerosol-forming substrate has a flow rate that is within about 0.5 microliters per second to about 2 microliters per second.

The cartridge may include a piston connected to the movable wall and a lead screw configured to connect the piston to a drive shaft and further configured to translate a rotation of the drive shaft into an axial movement of the piston and a corresponding axial movement of the movable wall.

The liquid storage portion may include a one-way valve connected to the outlet of the liquid storage portion.

BRIEF DESCRIPTION OF THE DRAWINGS

Example embodiments will now be described, by way of example only, with reference to the accompanying drawings, in which.

DETAILED DESCRIPTION

Figure 1A:
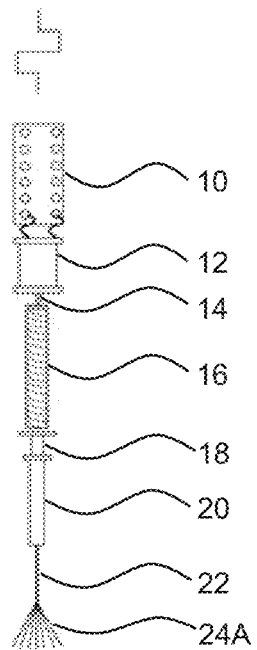
FIG. 1A is a topside view of an aerosol-generating system according to some example embodiments.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, and/or elements, but do not preclude the presence or addition of one or more other features, integers, steps, operations, elements, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, regions, layers and/or sections, these elements, regions, layers and/or sections should not be limited by these terms. These terms are only used to distinguish one element, region, layer or section from another region, layer or section. Thus, a first element, region, layer or section discussed below could be termed a second element, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Some example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to some example embodiments, an aerosol-generating system may include a liquid storage portion for storing liquid aerosol-forming substrate, wherein the liquid storage portion comprises a movable wall and an outlet, a vaporizer comprising a heating element having a structure defining an open-ended internal passage, a pump configured to deliver liquid aerosol-forming substrate from the outlet of the liquid storage portion to the internal passage of the heating element, the pump comprising a micro stepper motor with a drive shaft that is configured to rotate for a particular (or, alternatively, predetermined) amount upon performing one step of the micro stepper motor, a piston connected to the movable wall, and a lead screw connecting the drive shaft to the piston and configured to translate a rotation of the drive shaft into an axial movement of the piston and a corresponding axial movement of the movable wall, wherein the vaporizer is configured for heating the delivered liquid aerosol-forming substrate at the internal passage to a temperature sufficient to volatilize at least a part of the delivered liquid aerosol-forming substrate.

A determined amount of liquid aerosol-forming substrate may be pumped from the liquid storage portion to the internal passage of the heating element. Based on the liquid aerosol-forming substrate being deposited to the heating element directly, the liquid aerosol-forming substrate can remain in a liquid state until it reaches the heating element. Consequently, few residues may be produced during liquid transport of the liquid aerosol-forming substrate to the heating element. Such a design can allow for production of cartridges without vaporizers. Due to the improved liquid transport, tubing segments and vaporizers might not need to be disposed once the liquid storage portion is empty. By including a pump instead of a capillary wick or any other passive medium to draw liquid, only the actually required amount of liquid aerosol-forming substrate may be transported to the heating element. In some example embodiments, the aerosol-generating system may pump liquid aerosol-forming substrate based on a command signal (e.g., "on-demand"), for example in response to a drawing of air at least partially through the liquid aerosol-forming substrate.

The implementation of the pump by a micro stepper motor and a lead screw may permit miniaturization as compared to prior micro pump designs. As the liquid aerosol-forming substrate may never have to enter and exit the pump, a number ("quantity") of potential failure modes, including clogging and/or priming of the pump, may be reduced and/or prevented. Furthermore, as compared to piezo micro pump designs, the programming of the micro stepper motor may be far less complex so that the aerosol-generating system may include simpler electronic circuitry.

In contrast to some micro pump designs, backflow of the pumped liquid aerosol-forming substrate may be reduced and/or eliminated, for example unless the micro stepper motor is operated in reverse mode to actively pull back liquid aerosol-forming substrate.

The micro stepper motor may be configured to enable on-demand delivery of liquid aerosol-forming substrate for example at a low flow rate of approximately 0.5 to 2 microliters per second for intervals of variable or constant duration. The micro stepper motor may be configured to precisely actuate the piston for a determined micro distance in order to deliver a particular (e.g., determined) amount of liquid aerosol-forming substrate to the heating element. The amount of liquid aerosol-forming substrate pumped by the micro stepper motor can be precisely adjusted, as the movement of the piston may be based on the pitch of the turning lead screw. Consequently, the amount of deposited liquid aerosol-forming substrate may be determined from the amount ("quantity") of micro stepper motor pulses.

Both the micro stepper motor and the heating element may be configured to be triggered by a sensor. In some example embodiments, the micro stepper motor and the heating element may be triggered based on adult vaper interaction with an interface of the aerosol-generating system (e.g., a button, held for the duration of a drawing of air into the aerosol-generating system).

The micro stepper motor may step less than 1 degree per pulse. If and/or when the micro stepper motor is configured to rotate 1 degree per pulse, the thread includes a pitch of 0.75 millimeter and a capsule includes a cross-section of 6 $mm^2$, liquid aerosol-forming substrate may be dispensed in increments of 0.0125 $mm^3$ (0.0125 µl) per pulse.

In some example embodiments, the liquid storage portion is configured such that the axial movement of the movable wall towards the liquid storage portion causes a reduction of the volume of the liquid storage portion for example so as to deliver a determined amount of liquid aerosol-forming substrate from the outlet of the liquid storage portion to the internal passage of the heating element upon performing one step of the micro stepper motor.

In some example embodiments, the micro stepper motor is further configured to perform a step in reverse direction, thereby increasing the volume of the liquid storage portion. Reversing between draws of air into the aerosol-generating system may be advantageous because liquid aerosol-forming substrate located in the transport system may be reversed back into the liquid storage portion.

In some example embodiments, the movable wall is configured to contain the liquid aerosol-forming substrate in the liquid storage portion for example so that the micro stepper motor and the piston are not in contact with the liquid aerosol-forming substrate. The liquid storage portion may comprise a syringe with a capsule, wherein the liquid aerosol-forming substrate that is stored within the volume of the capsule that is limited by the movable wall. The capsule may have a cylindrical or substantially cylindrical (e.g., cylindrical within manufacturing tolerances and/or material tolerances) shape.

In some example embodiments, the liquid storage portion is separated from the micro stepper motor, thereby having the possibility of a removable and throw-away liquid containing capsule. This would eradicate the need for the users to refill the liquid storage portion themselves.

In some example embodiments, the aerosol-generating system further comprises a chamber into which the liquid aerosol-forming substrate may be delivered, and wherein the heating element is arranged inside the chamber downstream of the outlet of the liquid storage portion.

As used herein, the terms 'upstream', 'downstream', 'proximal', 'distal', 'front' and 'rear', are used to describe the relative positions of components, or portions of components, of the aerosol-generating system in relation to the direction in which an adult vaper may draw air through the aerosol-generating system.

The aerosol-generating system may comprise an outlet end through which an aerosol may be drawn to exit the aerosol-generating system. The outlet end may also be referred to as the proximal end. An adult vaper may draw on the proximal or outlet end of the aerosol-generating system in order to draw an aerosol generated by the aerosol-generating system. The aerosol-generating system comprises a distal end opposed to the proximal or outlet end. The proximal or outlet end of the aerosol-generating system may also be referred to as the downstream end and the distal end of the aerosol-generating system may also be referred to as the upstream end. Components, or portions of components, of the aerosol-generating system may be described as being upstream or downstream of one another based on their relative positions between the proximal, downstream or outlet end and the distal or upstream end of the aerosol-generating system.

In some example embodiments, the aerosol-generating system further comprises a tubing segment through which the liquid aerosol-forming substrate may be delivered from the liquid storage portion to the vaporizer, and wherein the vaporizer is arranged downstream of an open end of the tubing segment. The tubing segment may be arranged to deliver the liquid aerosol-forming substrate directly to the heating element. The tubing segment may be arranged to deliver the liquid aerosol-forming substrate towards an open end of the internal passage in the heating element. The tubing segment may extend from the liquid storage portion in a direction towards an open end of the internal passage in the heating element. The vaporiser may be located downstream of and/or proximate to an open end of the tubing segment. The vaporiser may extend at least partially around a portion of the tubing segment.

The tubing segment, also referred to as tube, may be a nozzle. The tubing segment may comprise any appropriate material, for example glass, silicon, metal, for example stainless steel, or plastics material, for example PEEK. For example, the tube may have a diameter of about 1 to 2 millimeters but other sizes are possible. In some example embodiments, the tubing segment comprises a capillary tube. The cross-section of the capillary tube may be circular, ellipsoid, triangular, rectangular or any other suitable shape to convey liquid. At least a width dimension of the cross-sectional area of the capillary tube may be sufficiently small such that capillary forces are present in the capillary tube. The cross-sectional area of the capillary tube may be sufficiently large such that a suitable amount of liquid aerosol-forming substrate can be conveyed to the heating element. In general, the cross-sectional area of the capillary tube may be less than 4 square millimeters, less than 1 square millimeter, and/or less than 0.5 square millimeters.

The vaporizer may comprise a heating coil extending from the tubing segment in a longitudinal direction with regard to the tubing segment (e.g., along a longitudinal axis of at least the tubing segment). In some example embodiments, the heating element, which may be a coil, may extend around a portion of the tubing segment. The portion may be a limited portion of the tubing segment. In some example embodiments, the vaporizer may comprise a heating coil extending in a longitudinal direction with regard to the aerosol-generating system (e.g., along a longitudinal axis of at least the aerosol-generating system). In some example embodiments, the heating coil may be mounted transverse to the tubing segment. The heating coil may overlap with the open end of the tubing segment for up to 3 millimeters, and/or for up to 1 millimeter. In some example embodiments, there may be a distance between the open end of the tubing segment and the heating coil. The length of the heating coil may be 2 millimeters to 9 millimeters, and/or 3 millimeters to 6 millimeters. The diameter of the heating coil may be such that one end of the heating coil can be mounted around the tubing segment. The diameter of the heating coil may be 1 millimeter to 5 millimeters, and/or 2 millimeters to 4 millimeters.

The vaporizer may comprise a conical heater extending from the tubing segment in a longitudinal direction (e.g., along a longitudinal axis of the conical heater, vaporizer aerosol-generating system, some combination thereof, or the like). The conical heater may overlap with the open end of the tubing segment in the longitudinal direction. In some examples, there may be a distance of 0.1 millimeters to 2 millimeters between the open end of the tubing segment and the conical heater, and/or 0.1 millimeters to 1 millimeter. The slant height of the conical heater may be 2 millimeters to 7 millimeters, and/or 2.5 millimeters to 5 millimeters. The diameter of the conical heater in cross-sectional view increases, when following the slant height from one end to the other, from a first diameter to a second diameter. The first diameter may be 0.1 millimeters to 2 millimeters, and/or 0.1 millimeters to 1 millimeter. The second diameter may be 1.2 millimeters to 3 millimeters, and/or 1.5 millimeters to 2 millimeters. In some example embodiments, the conical heater is configured to enable the liquid aerosol-forming substrate exiting from the tubing segment to pass the conical heater at the first diameter before the second diameter. The first diameter of the conical heater may be chosen such that one end of the conical heater can be mounted around the tubing segment.

The vaporizer may comprise a solid or a mesh surface. The vaporizer may comprise a mesh heater. The vaporizer may comprise an arrangement of filaments.

The vaporizer may comprise at least one of a solid, flexible, porous, and perforated substrate onto which the heating element may be at least one of mounted, printed, deposited, etched, and laminated. The substrate may be a polymeric or ceramic substrate.

In some example embodiments, the liquid storage portion comprises a one-way valve connected to the outlet of the liquid storage portion.

In some example embodiments, the flow rate of the liquid aerosol-forming substrate delivered through the outlet of the liquid storage portion is within 0.5 to 2 microliters per second.

In some example embodiments, the aerosol-generating system comprises a main assembly and a cartridge, wherein the cartridge is removably coupled to the main assembly, wherein the main assembly comprises a power supply, wherein the liquid storage portion is provided in the cartridge, and wherein the micro stepper motor is provided in the main assembly. In some example embodiments, the main assembly further comprises the vaporizer. The main assembly may comprise a tubing segment.

The aerosol-generating system according to some example embodiments may further comprise electric circuitry connected to the vaporizer and to an electrical power source, the electric circuitry configured to monitor the electrical resistance of the vaporizer, and to control the supply of power to the vaporizer based on the electrical resistance of the vaporizer.

The electric circuitry may comprise a controller with a microprocessor, which may be a programmable microprocessor, processor, etc. The electric circuitry may comprise further electronic elements. The electric circuitry may be configured to regulate a supply of power to the vaporizer. Power may be supplied to the vaporizer continuously following activation of the system or may be supplied intermittently, such as on a draw-by-draw basis. The power may be supplied to the vaporizer in the form of pulses of electrical current.

The electric circuitry may include a processor and a memory. The memory may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor may be, a central processing unit (CPU), a controller, or an application-specific integrated circuit (ASIC), that when, executing instructions stored in the memory, configures the processor as a special purpose computer to perform the operations of the electric circuitry. Such operations performed by the electric circuitry may include controlling a supply of electrical power from a power supply of the aerosol-generating system to one or more of a pump of the aerosol-generating system and one or more elements (e.g., a heating element) of a vaporizer of the aerosol-generating system.

The aerosol-generating system may comprise a power supply, e.g., a battery, within the main body (e.g., main assembly) of the housing. In some example embodiments, the power supply may be another form of charge storage device such as a capacitor. The power supply may be configured to be recharged and may have a capacity that enables the storage of enough energy for one or more vapings; for example, the power supply may have sufficient capacity to allow for the continuous generation of aerosol for a period of around six minutes or for a period that is a multiple of six minutes. In some example embodiments, the power supply may have sufficient capacity to allow for a particular (or, alternatively, predetermined) number of vapings or discrete activations of the heater assembly.

The aerosol-generating system may include a wall of the housing thereof, where the wall is configured to enable ambient air to enter the aerosol-generating system. The wall may be a wall opposite the vaporizer, and may be a bottom wall. The wall may include at least one semi-open inlet. The semi-open inlet may be configured to direct air to enter the aerosol-generating system and may further be configured to restrict air and/or liquid from leaving the aerosol-generating system through the semi-open inlet. A semi-open inlet may for example be a semi-permeable membrane, permeable in one direction only for air, but is air- and liquid-tight in the opposite direction. A semi-open inlet may for example also be a one-way valve. In some example embodiments, the semi-open inlets allow air to pass through the inlet if specific conditions are met, for example a minimum depression in the aerosol-generating system or a volume of air passing through the valve or membrane.

The liquid aerosol-forming substrate is a substrate configured to release volatile compounds that can form an aerosol. The volatile compounds may be released by heating the liquid aerosol-forming substrate. The liquid aerosol-forming substrate may comprise plant-based material. The liquid aerosol-forming substrate may comprise tobacco. The liquid aerosol-forming substrate may comprise a tobacco-containing material containing volatile tobacco flavor compounds, which are released from the liquid aerosol-forming substrate upon heating. The liquid aerosol-forming substrate may alternatively comprise a non-tobacco-containing material. The liquid aerosol-forming substrate may comprise homogenized plant-based material. The liquid aerosol-forming substrate may comprise homogenized tobacco material. The liquid aerosol-forming substrate may comprise at least one aerosol-former. The liquid aerosol-forming substrate may comprise other additives and ingredients, such as flavorants.

The aerosol-generating system may be an electrically operated vaping device. In some example embodiments, the aerosol-generating system is portable. The aerosol-generating system may have a total length between approximately 30 millimeters and approximately 150 millimeters. The aerosol-generating system may have an external diameter between approximately 5 millimeters and approximately 30 millimeters.

According to some example embodiments, a cartridge for the aerosol-generating system comprises the liquid storage portion, the piston, and the lead screw. The lead screw comprises an opening that is configured to receive the drive shaft of the micro stepper motor. In some example embodiments, the outlet of the liquid storage portion is configured to receive a tubing segment through which liquid aerosol-forming substrate is delivered to the deposition region of the heating element.

In some example embodiments, the cartridge comprises a first cover that covers at least one of the movable wall of the liquid storage portion, the piston, and the lead screw before inserting the cartridge into the main assembly. The first cover may be a pulled sticker or a seal, for example a film seal, to protect the cartridge before vapings, so that the movable wall cannot be accidently pushed before insertion into the main assembly. The first cover could be removed from the cartridge manually before inserting the cartridge into the main assembly. In some example embodiments, the first cover is configured to be punctured or pierced so that the first cover opens automatically upon the cartridge being inserted into the main assembly.

In some example embodiments, the cartridge further comprises a second cover that covers the outlet of the liquid storage portion before inserting the cartridge into the main assembly. The second cover may be a pulled sticker or a seal, for example a film seal, that is configured to protect the cartridge before use, so that the outlet cannot be accidently damaged before insertion of the cartridge into the main assembly. The second cover may be configured to be manually removed from the cartridge by hand before the cartridge is inserted into the main assembly. In some example embodiments, the second cover is configured to be punctured or pierced so that the second cover opens automatically upon the cartridge being inserted into the main assembly.

The cartridge may be a disposable article configured to be replaced with a new cartridge once the liquid storage portion of the cartridge is empty or below a minimum volume threshold. In some example embodiments, the cartridge is pre-loaded with liquid aerosol-forming substrate. The cartridge may be refillable.

The cartridge and its components, including the lead screw, the piston, and the movable wall, may be made of (e.g., may at least partially comprise) thermoplastic polymers, such as polyether ether ketone (PEEK).

In some example embodiments, a method for generating aerosol may include: (i) storing liquid aerosol-forming substrate in a liquid storage portion that comprises a movable wall and an outlet, (ii) delivering liquid aerosol-forming substrate from the outlet of the liquid storage portion to internal passage defined by a heating element of a vaporizer, wherein the delivering comprises actuating a micro stepper motor for performing one step so as to rotate a drive shaft of the micro stepper motor for a particular (or, alternatively, predetermined) amount, wherein a lead screw is connected to the drive shaft, the lead screw is connected to a piston, the piston is connected to the movable wall so as to translate a rotation of the drive shaft into an axial movement of the piston and a corresponding axial movement of the movable wall, and (iii) heating the delivered liquid aerosol-forming substrate in the internal passage to a temperature sufficient to volatilize ("vaporize") at least a part of the delivered liquid aerosol-forming substrate.

FIG. 1A shows an aerosol-generating system comprising electric circuitry 10 that drives a micro stepper motor 12 with a drive shaft 14. Drive shaft 14 is coupled with a lead screw 16 that translates the rotational movement of the drive shaft 14 in response to an electrical pulse of the electric circuitry 10 to an axial movement. The lead screw 16 is connected to a piston 18 that moves a movable wall 26 (not shown in FIG. 1A) in capsule 20. Upon a pulse of the electric circuitry 10 to drive the micro stepper motor 12, the available volume in the capsule 20 is reduced by a particular (or, alternatively, predetermined) amount. The capsule 20 is filled with liquid aerosol-forming substrate. Due to the reduction of volume resulting from pulses, a corresponding amount of liquid aerosol-forming substrate flows into an open-ended nozzle 22 where the liquid aerosol-forming substrate leaves the nozzle via a jet 24A. The jet 24A causes aerosolization of the liquid aerosol-forming substrate.

Figure 1B:
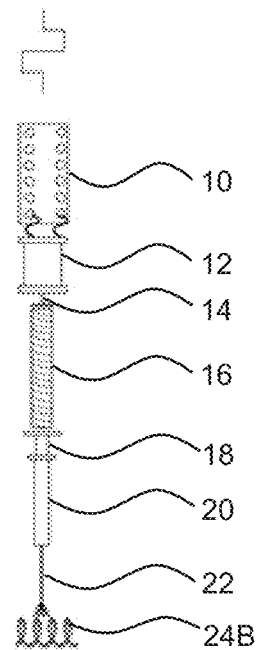
FIG. 1B is a topside view of an aerosol-generating system according to some example embodiments.
Figure 1C:
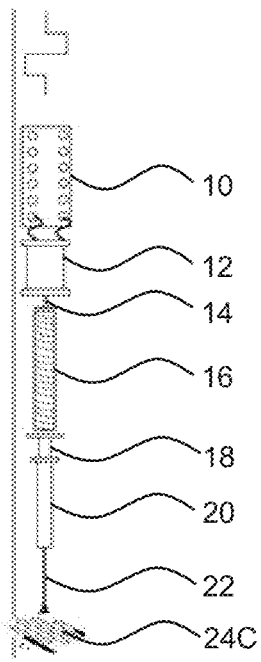
FIG. 1C is a topside view of an aerosol-generating system according to some example embodiments.
Figure 1D:
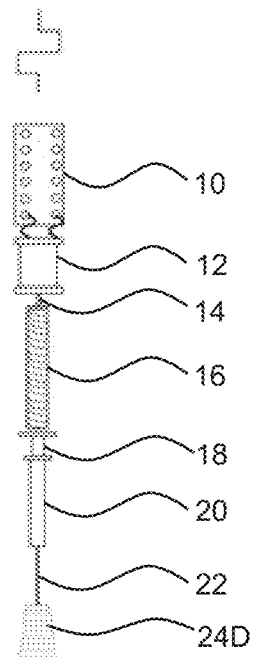
FIG. 1D is a topside view of an aerosol-generating system according to some example embodiments.

FIGS. 1B, 1C, and 1D show aerosol-generating systems with a different handling of the liquid aerosol-forming substrate once the liquid aerosol-forming substrate exits the nozzle 22.

In some example embodiments, including the example embodiments shown in FIG. 1B, a heating coil 24B is located downstream of and/or proximate to the nozzle 22 and is configured to directly heat the liquid aerosol-forming substrate that exits the nozzle 22.

In some example embodiments, including the example embodiments shown in FIG. 1C, a flat heater 24C with a liquid permeable structure is located downstream of and/or proximate to the nozzle 22 and is configured to directly heat the liquid aerosol-forming substrate that exits the nozzle 22.

In the some example embodiments, including the example embodiments shown in FIG. 1D, a conical heater 24D is located downstream of the nozzle 22 and is configured to directly heat the liquid aerosol-forming substrate that exits the nozzle 22.

Figure 2:
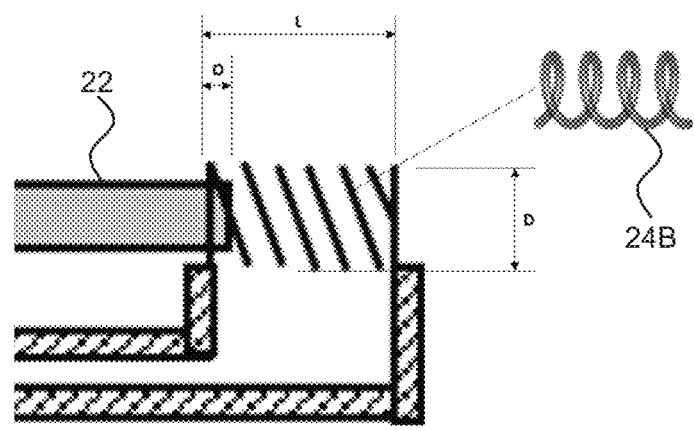
FIG. 2 is a topside view of a tubing segment and a heating coil for an aerosol-generating system according to some example embodiments.

FIG. 2 shows a detail of the open ended side of the nozzle 22 according to some example embodiments. In some example embodiments, including the example embodiments shown in FIG. 2, a heating coil 24B is mounted onto the open ended side of the nozzle 22 such that the heating coil 24B extends from the nozzle 22 in longitudinal direction. Liquid aerosol-forming substrate may exit at the open end of the nozzle 22. One or more surfaces of the heating coil 24B may at least partially define an internal passage that extends through an interior space defined by the heating coil 24B. As referred to herein, an "internal passage" may include an "open-ended internal passage." An aerosol-generating system may be configured to direct liquid aerosol-forming substrate to the open-ended internal passage. For example, the nozzle 22 may be configured to direct the liquid aerosol-forming substrate to the internal passage. The heating coil 24B may be configured to at least partially overlap the nozzle 22 and may be configured to extend over and around a space defined by the nozzle 22 and extending outwards from the open-ended side of the nozzle 22, such that the liquid aerosol-forming substrate is directly heated. The heating coil 24B has a length L, a diameter D and an overlap O with the nozzle 22.

Figure 3A:
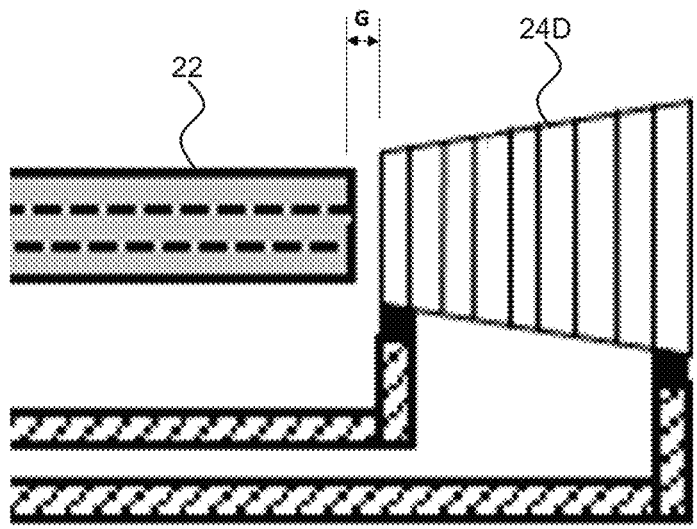
FIG. 3A is a topside view of a tubing segment and a conical heater for an aerosol-generating system according to some example embodiments.

FIG. 3A shows a detail of the open ended side of the nozzle 22. A conical heater 24D is mounted downstream the open ended side of the nozzle 22 such that the conical heater 24D extends from the nozzle 22 in longitudinal direction. Liquid aerosol-forming substrate may exit at the open end of the nozzle 22. The conical heater 24D may define an internal passage, including an open-ended internal passage. The conical heater 24D may be configured to at least partially overlap the nozzle 22 and may be configured to extend over and around a space defined by the nozzle 22 and extending outwards from the open-ended side of the nozzle 22, such that the liquid aerosol-forming substrate is directly heated. There is a distance G between the cone end side of the conical heater 24D and the nozzle 22.

Figure 3B:
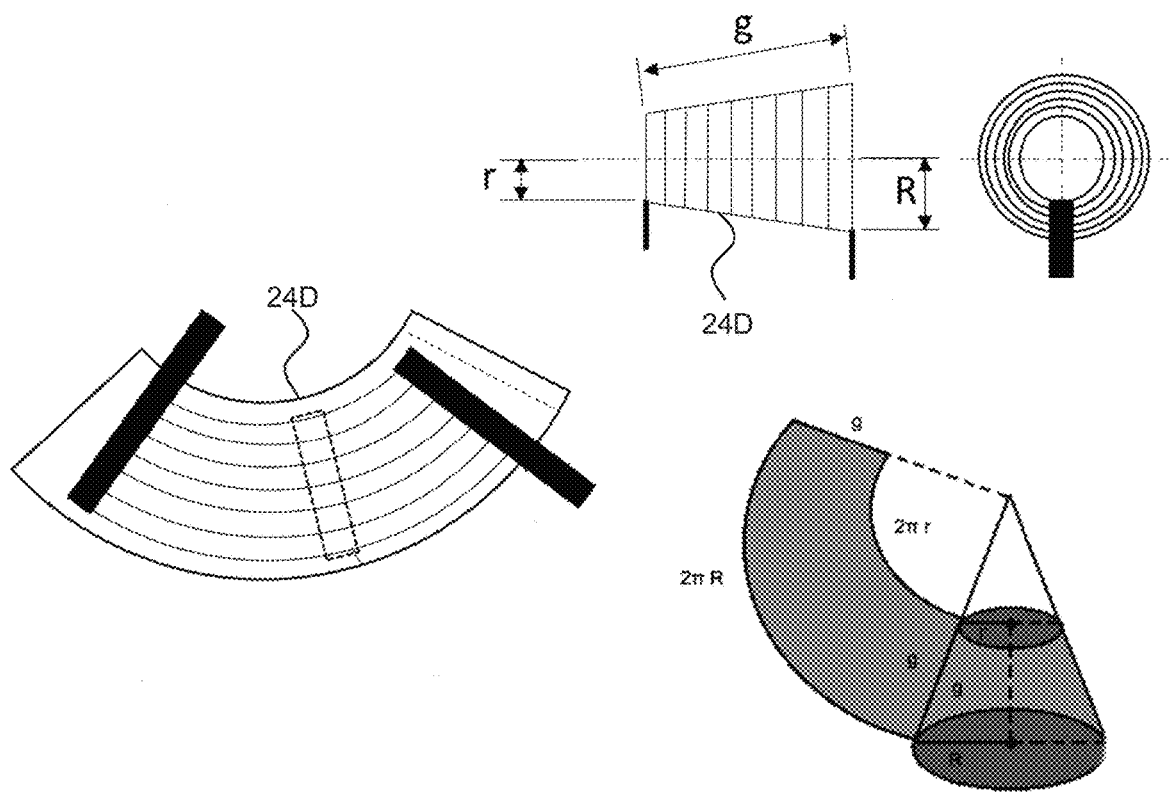
FIG. 3B is schematic illustration illustrating making the conical heater shown in FIG. 3A.

FIG. 3B is a schematic illustration of an operation of making the conical heater 24D from a flat substrate. The conical heater 24D has a slant height g with a radius that increases from a first radius r to a second radius R.

Figure 4:
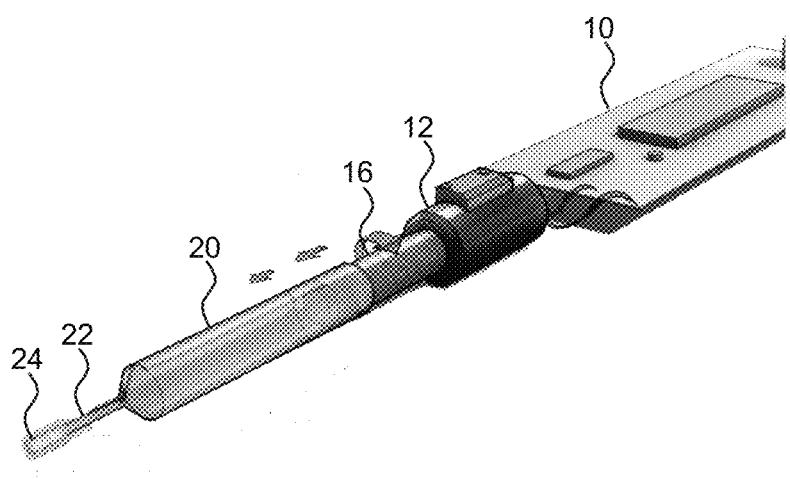
FIG. 4 is a schematic illustration of a perspective view of an aerosol-generating system according to some example embodiments.

FIG. 4 shows the aerosol-generating systems of FIGS. 1B, 1C, and 1D in a perspective view with a heating element 24 downstream the tubing segment 22.

Figure 5:
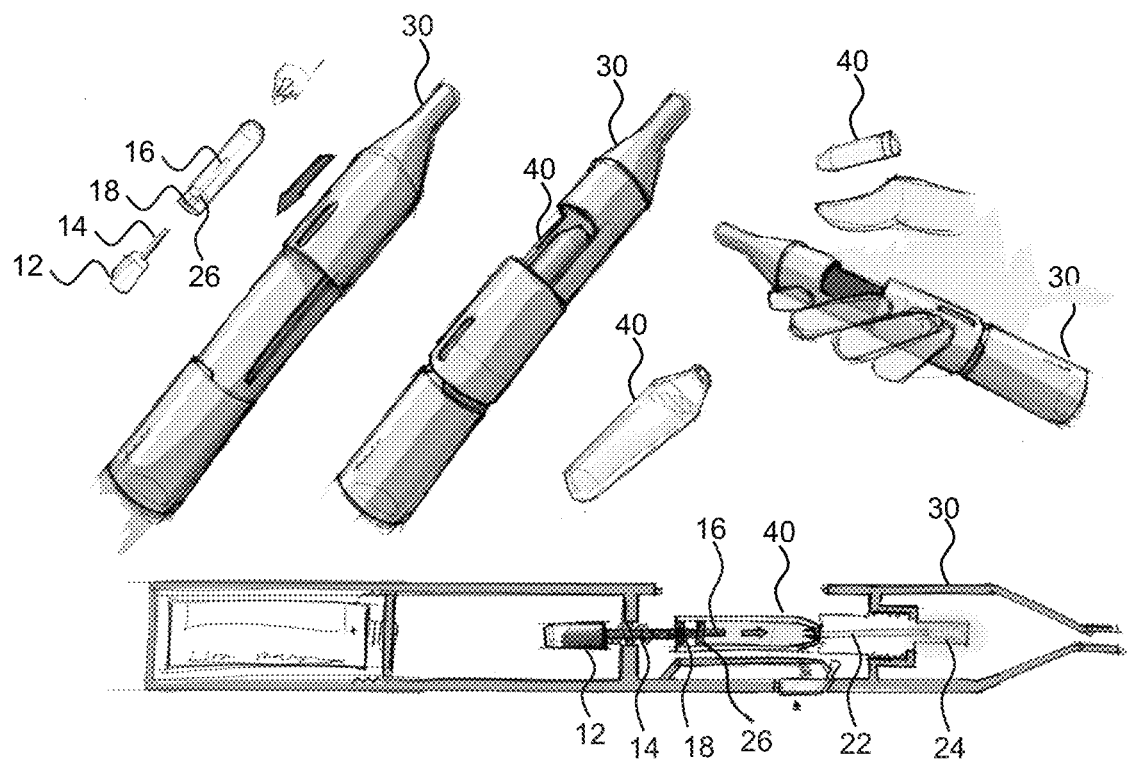
FIG. 5 is a schematic illustration of a perspective view and a cross-sectional view of an aerosol-generating system according to some example embodiments.

FIG. 5 is a schematic illustration of an aerosol-generating system. The aerosol-generating system comprises a main assembly 30 and a separate cartridge 40. The main assembly 30 comprises a micro stepper motor 12 with a drive shaft 14. The cartridge 40 comprises a capsule that includes the liquid storage portion. The main assembly 30 further comprises a tubing segment 22 and a vaporizer 24 configured to receive liquid aerosol-forming substrate via the tubing segment 22 that extends from the liquid storage portion towards the vaporizer 24. The vaporizer 24 is configured to heat the liquid aerosol-forming substrate directly after the liquid aerosol-forming substrate exits the tubing segment 22.

Furthermore, the cartridge 40 comprises a lead screw 16 coupled to the drive shaft 14 and a piston 18 that is configured to be axially moved by the lead screw 16. The liquid storage portion comprises a movable wall 26 that separates the liquid storage portion from the remaining components inside the capsule of the cartridge.

The cartridge 40 is configured to be received in a cavity within the main assembly 30. Cartridge 40 may be configured to be replaceable from the main assembly 30. The cartridge 40 may be replaced if and/or when the aerosol-forming substrate provided in the cartridge 40 is depleted. The main assembly 30 may include a slider that is configured to be moved to expose the cavity if and/or when a new cartridge 40 is inserted into the main assembly 30. A new cartridge 40 may be inserted into the exposed cavity. The lead screw 16 of the cartridge 40 comprises an opening configured to receive the drive shaft 14 of the micro stepper motor 12. The capsule of the cartridge 40 comprises an outlet configured to receive an end of the tubing segment 22. As depicted in FIG. 5, the cartridge 40, the lead screw 16, the piston 18, the movable wall 26, and the micro stepper motor 12, including the drive shaft 14 of the micro stepper motor 12, are in longitudinal alignment along a longitudinal axis of the main assembly 30 when the cartridge 40 is inserted into the main assembly 30.

The main assembly 30 is portable and may comprise a main body and an outlet-end insert. The main assembly 30 includes a power supply, for example a battery such as a lithium iron phosphate battery, electronic circuitry 10, and a cavity. Electrical connectors are provided at the sides of the main body and are configured to provide an electrical connection between the electric circuitry 10 and the battery. The outlet-end insert comprises a plurality of air inlets and an outlet. In some example embodiments, an adult vaper may draw on the outlet to draw air into the air inlets, through an interior of at least a portion of the aerosol-generating system, through the outlet-end insert to the outlet, and thereafter into the mouth or lungs of the user. Internal baffles may be included in the main assembly 30 and may be configured to force the air flowing through the outlet-end insert to flow past the cartridge 40.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An aerosol-generating device, comprising:
a chamber configured to receive a removable liquid aerosol-forming substrate storage portion having a movable wall;
a vaporizer including a heating element having a structure defining an open-ended internal passage;
a pump configured to deliver a liquid aerosol-forming substrate from the removable liquid aerosol-forming substrate storage portion to the open-ended internal passage of the heating element, the pump including
a micro stepper motor,
a drive shaft extending from the micro stepper motor into the chamber, the drive shaft configured to connect with the removable liquid aerosol-forming substrate storage portion at the movable wall, and
a lead screw configured to connect the drive shaft to the movable wall of the removable liquid aerosol-forming substrate storage portion and further configured to translate a rotation of the drive shaft into an axial movement of the movable wall;
a power supply configured to supply electrical power to the vaporizer and the pump; and
a nozzle configured to direct the liquid aerosol-forming substrate from the removable liquid aerosol-forming substrate storage portion to the vaporizer, the nozzle being located proximate to the pump,
wherein the removable liquid aerosol-forming substrate storage portion is configured to be inserted into the chamber, the removable liquid aerosol-forming substrate storage portion including
the movable wall configured to connect with the lead screw of the pump,
a liquid storage portion, and
an outlet configured to allow liquid aerosol-forming substrate to exit the liquid storage portion,
wherein the removable liquid aerosol-forming substrate storage portion and the pump are collectively configured to pump a particular amount of the liquid aerosol-forming substrate from the outlet of the removable liquid aerosol-forming substrate storage portion to the heating element upon activation of the micro stepper motor.

2. The aerosol-generating device of claim 1, wherein the chamber includes at least one movable wall.

3. The aerosol-generating device of claim 1, wherein the heating element is conically shaped.

4. The aerosol-generating device of claim 1, wherein the heating element overlaps the nozzle by 3 millimeters or less.

5. The aerosol-generating device of claim 1, wherein the heating element is spaced apart from the nozzle.

6. The aerosol-generating device of claim 1, wherein the nozzle is in longitudinal alignment with the heating element.

7. The aerosol-generating device of claim 1, wherein an inner cross-sectional area of the nozzle is less than 4 square millimeters.

8. The aerosol-generating device of claim 1, further comprising:
 a one-way valve connected to the removable liquid aerosol-forming substrate storage portion.

9. The aerosol-generating device of claim 1, wherein the heating element may be mounted transverse to the nozzle.

10. The aerosol-generating device of claim 1, further comprising:
 a first cover that is configured to cover the movable wall of the removable liquid aerosol-forming substrate storage portion prior to the removable liquid aerosol-forming substrate storage portion being inserted into the aerosol-generating device.

11. The aerosol-generating device of claim 10, further comprising:
 a second cover that is configured to cover the outlet of the liquid storage portion of the removable liquid aerosol-forming substrate storage portion prior to inserting the removable liquid aerosol-forming substrate storage portion into the aerosol-generating device.

12. The aerosol-generating device of claim 1, wherein the micro stepper motor is further configured to perform a step in a reverse direction, such that an internal volume of the liquid storage portion is increased.

13. A method for generating aerosol, comprising:
 storing a liquid aerosol-forming substrate in a cartridge, the cartridge including a liquid storage portion, a movable wall, and an outlet;
 inserting the cartridge into an aerosol-generating device that includes a pump, the pump further including a micro stepper motor having a drive shaft and a lead screw, such that
  the cartridge is positioned proximally to the pump, and
  the outlet of the liquid storage portion is configured to direct a flow of liquid-aerosol substrate from the cartridge to a vaporizer of the aerosol-generating device; and
 pumping the liquid aerosol-forming substrate from the outlet of the liquid storage portion to the vaporizer upon activation of the micro stepper motor, the pumping including
  the lead screw translating a rotation of the drive shaft of the micro stepper motor into an axial movement of the movable wall, and
  axially moving the movable wall toward the liquid storage portion to cause a particular amount of the liquid aerosol-forming substrate to be pumped from the outlet of the cartridge to the vaporizer of the aerosol-generating device, causing a reduction of a volume of the liquid storage portion.

14. The method according to claim 13, further comprising:
 causing the micro stepper motor to perform a step in a reverse direction, such that an internal volume of the liquid storage portion is increased.

\* \* \* \* \*